United States Patent [19]

Ax et al.

[11] Patent Number: 4,767,703
[45] Date of Patent: Aug. 30, 1988

[54] METHOD FOR ASSESSING THE FERTILITY OF MALE MAMMALS

[75] Inventors: Roy L. Ax, Mazomanie, Wis.; Richard W. Lenz, Tunkhannock, Pa.

[73] Assignee: Wisconsin Alumni Research Foundation, Madison, Wis.

[21] Appl. No.: 596,327

[22] Filed: Apr. 3, 1984

[51] Int. Cl.$^4$ .............................................. C12Q 1/02
[52] U.S. Cl. ........................................ 435/29; 435/4; 435/806; 436/63; 436/906
[58] Field of Search ........................ 435/2, 4, 29, 806; 436/63, 906

[56] References Cited

PUBLICATIONS

Schill et al.—Chem. Abst. vol. 86 (1977), p. 184,948v.
Schill et al.—Chem. Abst. vol. 82 (1975), p. 41199h.
Good Pasture—Chem. Abst. vol. 94 (1981), p. 13738n.
J. H. D. Bryan and S. R. Akruk (1977), A Naphthol Yellow S and Erythrosin B Staining Procedure for Use in Studies of the Acrosome Reaction of Rabbit Spermatozoa, *Stain Technol.*, 52, 47–50.
R. C. Jones (1973), Preparation of Spermatozoa for Electron and Light Microscopy, *J. Reprod. Fertil.*, 33, 145–149.
W. Byrd (1981), In Vitro Capacitation and the Chemically Induced Acrosome Reaction in Bovine Spermatozoa, *J. Exp. Zool.*, 215, 35–46.
J. M. Bedford (1970), Sperm Capacitation and Fertilization in Mammals, *Biol. Reprod.*, Suppl. 2, 128–158.
S. Aonuma et al. (1973), Studies on Sperm Capacitation: I. The Relationship Between a Guinea-Pig Sperm–Coating Antigen and a Sperm Capacitation Phenomenom, *J. Reprod. Fertil.*, 35, 425–432.
D. W. Fawcett (1975), The Mammalian Spermatozoon, *Dev. Biol.*, 44, 394–436.
R. Yanagimachi (1978), Sperm-egg Association in Mammals, *Curr. Top. Dev. Biol.*, 12, 83–105.
T. J. Wincek et al. (1979), Fertilization: A Uterine Glycosaminoglycan Stimulates the Conversion of Sperm Proacrosin to Acrosin, *Science*, 203, 553–554.
R. F. Parrish et al. (1980), Glycosaminoglycan Stimulation of the in vitro Conversion of Boar Proacrosin into Acrosin, *J. Androl.*, 1, 89–95.
R. B. L. Gwatkin and O. F. Andersen (1969), Capacitation of Hamster Spermatozoa by Bovine Follicular Fluid, *Nature*, (Lond.), 224, 1111–1112.
H. J. Grimek and R. L. Ax (1982), Chromatographic Comparison of Chondroitin-Containing Proteoglycan from Small and Large Bovine Ovarian Follicles, *Biochem. Biophys. Res. Comm.*, 104, 1401–1406.
R. W. Lenz et al. (1982), Proteoglycan from Bovine Follicular Fluid Enhances an Acrosome Reaction in Bovine Spermatozoa, *Biochem. Biophys. Res. Comm.*, 106, 1092–1098.
R. R. Handrow et al. (1982), Structural Comparisons Among Glycosaminoglycans to Promote an Acrosome Reaction in Bovine Spermatozoa, *Biochem. Biophys. Res. Comm.*, 107, 1326–1332.

(List continued on next page.)

*Primary Examiner*—Sam Rosen
*Attorney, Agent, or Firm*—David J. Houser

[57] ABSTRACT

A method for evaluating the fertility of a male mammal. A semen sample is obtained from the individual to be tested. The sperm is separated from the seminal plasma of the semen sample. At least one test portion and a control portion of the sperm are isolated. The sperm portions are incubated, the test portion being exposed to a glycosaminoglycan in a concentration effective to induce an acrosome reaction in sperm. A representative sample of incubated sperm from each portion is then counted by means of observation by light microscopy to measure the increase in acrosome reaction in the test portions as compared to the control portion. A kit is provided for the convenient performance of the method. The kit includes a supply of sterile liquid culture medium, sterile closable culture vessels, and a supply of selected, sterile GAG meterable substantially aseptically in known amounts into each culture vessel used as a test vessel.

9 Claims, 1 Drawing Sheet

PUBLICATIONS

P. V. Dandekar and M. Gordon (1975), Electron Microscope Evaluation of Rabbit Eggs Exposed to Spermatozoa Treated with Capacitating Agents, *J. Reprod. Fertil.*, 44, 143–146.

K. T. Kirton and H. D. Hafs (1965), Sperm Capacitation by Uterine Fluid or B-Amylase in vitro, *Science*, 150, 618–619.

A. Rosado et al. (1974), Capacitation in vitro of Rabbit Spermatozoa with Cyclic Adenosine Monophosphate and Human Follicular Fluid, *Fertil. Steril.*, 25, 821–824.

J. M. Bedford (1969), Morphological Aspects of Sperm Capacitation in Mammals, *Adv. Biosci.*, 4, 35–50.

B. G. Brackett and G. Oliphant (1975), Capacitation of Rabbit Spermatozoa in vitro, *Biol. Reprod.*, 12, 260–274.

T. Iwamatsu and M. C. Chang (1969), in vitro Fertilization of Mouse Eggs in the Presence of Bovine Follicular Fluid, *Nature*, 224, 919–920.

B. D. Bavister and R. Yanagimachi (1977), The Effects of Sperm Extracts and Energy Sources on the Motility and Acrosome Reaction of Hamster Spermatozoa in vitro, *Biol. Reprod.*, 16, 228–237.

W. B. Schill, *Fert. Ster.* (1974), 25: 703–712.

Goodpasture et al., *J. Androl.* (1980), 1: 16–27.

Goodpasture et al., *J. Reprod. Fert.* (1981), 63: 397–405.

Goodpasture et al., *J. Androl.* (1982), 3: 151–156.

METHOD FOR ASSESSING THE FERTILITY OF MALE MAMMALS

TECHNICAL FIELD

The present invention relates to the determination of the fertility of male mammals in general and, in particular, to such a determination of fertility by light microscopic examination of sperm.

BACKGROUND OF ART

In various contexts, it is useful to be able to determine the fertility of a male mammal. Thus, while the artificial insemination industry is concerned with the genetic makeup of individuals resulting from artificial insemination of females, it is also importantly interested in the likelihood that fertilization will take place in any event as a consequence of the artificial insemination of the female. For example, in the bovine artificial insemination industry, bulls are evaluated on the basis of the milk production of the daughters produced from the bull. However, if the fertility of the bull is low as measured by the number of times a cow must be artificially inseminated before pregnancy occurs, the value of the semen produced by the bull and therefore the value of the bull itself is low. If fertility is sufficiently low, such bulls are disposed of.

The costs resulting from inability to reliably predict fertility may be high. Currently in the bovine artificial insemination industry it takes from five to six years to detect and weed out low-fertility bulls, throughout which period the bull must be fed, housed, and otherwise cared for at considerable expense. When a breeder examines a one-year-old, sexually mature bull, the breeder's only source of information about the bull's fertility is the pedigree information available on the animal. Testicular size and other gross physical characteristics of the animal provide little or no useful information relating to fertility.

The first determination of the bull's general desirability conventionally relates to milk production. Typically the bull is bred to cows until a selected number of daughters are produced. Typically as many as 200 daughters are produced and carefully monitored. It may take as much as a year before so many daughters are produced, so that the bull is now two years old. Two additional years must then pass before the daughters themselves become sexually mature, can be impregnated, calve, and begin to produce milk. By this time the bull is approximately four years old. The lactation of the daughters is carefully monitored, and the quality of the daughters is thus evaluated. This process may take from 10 to 12 months. By this time the bull is five years old. At that time, a first decision is made as to whether to keep the bull for breeding purposes based on the quality of the milk production of daughters produced from the bull.

If the bull is kept, it is then included in the breeder's general breeding program. Only at that time is the breeding data sufficient to begin to judge the bull's fertility, as a large population of cows are inseminated with semen from the bull. By this time, the bull is almost six years old and has been held by the breeder for approximately five years after the bull had reached sexual maturity. If the bull is found to exhibit unacceptably low fertility, the breeder has spent a large amount of money and time with a low rate of return. This expenditure could have been saved had it been possible to evaluate the fertility of the bull back at the point that the bull had become sexually mature and before all of the testing relating to the milk production of the bull's daughters had been undertaken. Typically only one out of seven bulls are kept after evaluation of the bull's progeny and fertility has been completed. If at least some of the bulls eliminated could be detected as being of low fertility early in the evaluation process, considerable money could be saved.

In other contexts, it is also useful to evaluate quickly the fertility of a breeding male. Breeding males for various types of animals are sold for use with a farmer's herd or for addition to the stud string of an artificial inseminator. Those skilled in the art are aware of no means for evaluating the fertility of animals so sold unless statistical data have been amassed on the animal's past production. As a consequence, the purchase of such animals tends to be blind speculation at least with regard to fertility. The availability of a method for determining fertility in a short period of time could thus be of value both to the seller who desires to substantiate the reasonableness of a high price for his animal and to the buyer who wants to know in advance what he is getting.

In other contexts, tests for male fertility not dependent on monitoring actual impregnations would be advantageous. Thus, human fertility clinics can evaluate the sperm count of a male but have no effective current means of evaluating the capability of that sperm to fertilize an ovum in vivo. Similarly, it would be desirable to be able to evaluate the fertility of male zoo animals and other animals in which fertility cannot be determined conveniently, economically, or in a socially practical way by attempted fertilization of large numbers of females.

It is known to those skilled in the art that mammalian spermatozoa must reside for a time in the female reproductive tract before acquiring the capacity to fertilize ova. See J. M. Bedford (1970), Sperm Capacitation and Fertilization in Mammals. *Biol. Reprod.*, Suppl. 2, 128-158. The resulting effect upon spermatozoa is called "capacitation." Capacitation seems to require the removal of components from the spermatozoa which are epididymal or seminal plasmatic in origin. See S. Aonuma et al. (1973), Studies on Sperm Capacitation: I. The relationship between a guinea pig sperm coating antigen and a sperm capacitation phenomenom. *Reprod. Fertil.*, 35, 425-432. After capacitation has occurred, the sperm are able to undergo an acrosome reaction. The acrosome reaction releases enzymes that digest the matrix of the cumulus cells surrounding the ovum. This digestion of the matrix permits the zona pellucida to be penetrated by spermatozoa so that the sperm may make its way toward the ovum. See D. W. Fawcett (1975), The Mammalian Spermatozoon, *Dev. Biol.*, 44, 394-436; and R. Yanagimachi (1978), Sperm-egg Association in Mammals, *Curr. Top. Dev. Biol.*, 12, 83-105.

It is not known precisely what components of the female reproductive tract enhance the ability of sperm to undergo capacitation and the acrosome reaction. Porcine uterine fluid was found to stimulate conversion of sperm proacrosin to acrosin necessary to the acrosin reaction. See T. J. Wincek et al. (1979), Fertilization: A Uterine Glycosaminoglycan stimulates the conversion of sperm proacrosin to acrosin, *Science*, 203, 553-554. In the Wincek study, the active component of the uterine fluid was destroyed by testicular hyaluronidase or chondroitin ABC lyase, suggesting that a uterine glycosaminoglycan (hereinafter "GAG") was responsible. Commercially available GAGs have also been shown to accelerate conversion of proacrosin to acrosin. See R. F. Parrish et al. (1980), Glycosaminglycan Stimulation of the in vitro Conversion of Boar Proacrosin into Acrosin, *J. Androl.*, 1, 89–95.

Other materials are known to enhance capacitation or the acrosome reaction in spermatozoa. These include follicular fluid [See R. B. L. Gwatkin and D. F. Anderson (1969), Capacitation of Hamster Spermatozoa by Bovine Follicular Fluid, *Nature*, (Lond.), 224, 1111–1112.] and a chondroitin sulfate proteoglycan found in bovine follicles [H. J. Grimek and R. L. Ax (1982), Chromatographic Comparison of Chondroitin-containing Proteoglycan from Small and Large Bovine Ovarian Follicles, *Biochem. Biophys. Res. Comm.*, 104, 1401–1406; R. W. Lenz et al. (1982), Proteoglycan from Bovine Follicular Fluid Stimulates an Acrosome Reaction in Bovine Spermatozoa, *Biochem. Biophys. Res. Comm.*, 106, 1092–1098]. Lenz et al. in the article just cited showed that pretreatment of the proteoglycan with chondroitinase ABC prevented the effect from occurring, suggesting that the GAG side-chains may be a primary factor in the reaction. The GAGs heparin, chondroitin sulfates A, B, or C, and hyaluronic acid all promoted the occurrence of acrosome reactions in bovine sperm. The potencies were related to the degree of sulfation of the GAGs. See R. R. Handrow et al. (1982), Structural Comparisons Among Glycosaminoglycans to Promote an Acrosome Reaction in Bovine Spermatozoa, *Biochem. Biophys. Res. Comm.*, 107, 1326–1332.

In vitro capacitation of rabbit sperm has also been studied. With varying degrees of success, rabbit sperm capacitation has been obtained by treatment with trypsin [P. V. Dandekar and M. Gordon (1975), Electron Microscope Evaluation of Rabbit Eggs Exposed to Spermatozoa Treated with Capacitating Agents, *J. Reprod. Fertil.*, 44, 143–146], uterine fluid [K. T. Kirton and H. D. Hafs (1965), Sperm Capacitation by Uterine Fluid or B-amylase in vitro, *Science*, 150, 618–619], human or rabbit follicular fluid [A. Rosado et al. (1974), Capacitation in vitro of Rabbit Spermatozoa with Cyclic Adenosine Monophosphate and Human Follicular Fluid, *Fertil. Steril.*, 25, 821–824; J. M. Bedford (1969), Morphological Aspects of Sperm Capacitation in Mammals, *Adv. Biosci.*, 4, 35–50, respectively], and high ionic strength medium [B. G. Brackett and G. Oliphant (1975), Capacitation of Rabbit Spermatozoa in vitro, *Biol. Reprod.*, 12, 260–274.] In vitro capacitation and acrosome reaction of mouse spermatozoa has been obtained using bovine follicular fluid. See T. Iwamatsu and M. C. Chang (1969), In vitro Fertilization of Mouse Eggs in the Presence of Bovine Follicular Fluid, *Nature*, 224, 919–920.

Those skilled in the art are not cognizant of a method to verify the ability of spermatozoa to undergo an acrosome reaction by light microscopic examination of the spermatozoa. Furthermore, those skilled in the art are not cognizant of any method for determining the fertility of a male mammal by direct examination of sperm therefrom.

BRIEF SUMMARY OF THE INVENTION

The method of the invention is summarized in that a method for evaluating the fertility of a male mammal includes the steps of obtaining a semen sample from the individual to be tested. The sperm then is separated from the semen plasma. A test portion and a control portion of the sperm are isolated. The portions of sperm are incubated, with the test portion exposed to a selected glycosaminoglycan in a concentration effective to induce an acrosome reaction in the sperm of the test portion. Representative samples of the sperm from each portion are then counted by means of observation by light microscopy to measure the percent increase in acrosome reaction in the test portion as compared to the control portion.

The kit of the invention for use in evaluating fertility of a male mammal includes a supply of sterile liquid culture medium. The kit further includes sterile, closable culture vessels, including at least one control and one test vessel. A supply is included of selected, sterile GAG, meterable substantially aseptically in known amounts into each test vessel.

A primary object of the invention is to provide a method for evaluating the fertility of a male mammal by direct examination of the sperm thereof.

A second object of the invention is to provide for such a method utilizing light microscopy.

An additional object of the invention is to provide such a method that may be conveniently carried out without the availability of a laboratory of high sophistication.

A further object of the invention is to provide such a method adapted to detect infertility in a male mammal within a conveniently short period of time.

Another object of the invention is to provide a kit for use in assessing the fertility of male mammals.

Other objects, features, and advantages of the invention will be apparent from the following detailed description of a preferred embodiment of a method and reagent exemplifying the principles of the invention.

BRIEF DESCRIPTION OF THE DRAWINGS

The figures are graphical presentations of data discussed in the Detailed Description of the Preferred Embodiment.

DETAILED DESCRIPTION OF THE PREFERRED EMBODIMENT

Figure 1:
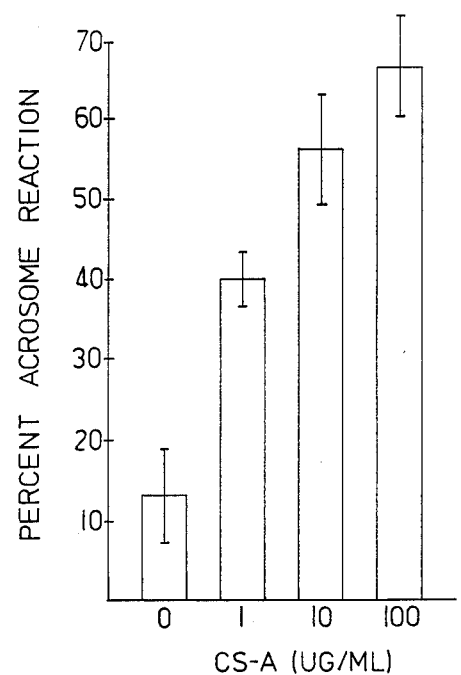

A method was developed for inducing an acrosome reaction in spermatozoa in vitro in response to treatment with any one or more of several GAGs. A visual test was developed for determining by light microscopy the extent to which spermatozoa have undergone an acrosome reaction. Finally, a correlation was made between the results of the visual test for acrosome reaction and fertility in male mammals.

In the experiments referred to below, the following GAGs were purchased from Sigma Chemical Company. Chondroitin A and C (CS-A, CS-C) were sodium salts of purified whale and shark cartilage, respectively. Chondroitin sulfate B (CS-B) was a sodium salt purified from porcine skin. Heparin was a grade II sodium salt isolated from porcine intestinal mucosa. Hyaluronic acid was a grade IV sodium salt isolated from bovine vitreous humor. Dextran sulfate was a sodium salt of a branched, sulfated polysaccharide used as an appropriate sulfated control.

In the exeriments referred to below, the GAG heperan sulfate was obtained from bovine follicular fluid by the following process. A thin layer of toluene was placed on the surface of the follicular fluid to prevent microbial growth. Then 0.01 units/ml of chondroitinase ABC was added to the follicular fluid, which was then incubated at 37° C. for four hours. Then 1 mg/ml of a protease enzyme was added to the follicular fluid, which was incubated for an additional eighteen to twenty-four hours at 37° C. The solution was made up to a final concentration of 5% trichloroacetic acid. This solution was centrifuged at 2000 g for approximately ten minutes. The supernatant was poured into three volumes of absolute ethanol and incubated overnight at 4° C. It was then centrifuged at 1000 to 2000 g for ten minutes. Heperan sulfate was left in the bottom of the centrifuge tube. The fluid was decanted and the heperan sulfate was then redissolved in water at a volume approximately 1/10 of the original volume of follicular fluid. Concentration and purity was verified by high production liquid chromatography.

Spermatozoa were obtained in the following ways. Bovine epididymides were obtained from Oscar Mayer Company, Madison, Wis. The material was obtained and processed promptly after slaughter of the animal. Each epididymis was surgical opened and its contents retrieved. The semen was diluted in the culture medium described below. The sperm were then separated from the semen plasma by centrifugation and resuspended in culture medium. The medium used was a modification of Tyrode's Balanced Salt Solutions (hereinafter TALP) as described by B. D. Bavister and R. Yangimachi (1977), The Effects of Sperm Extract and Energy Sources on the Motility and Acrosome Reaction of Hamster Sperm in vitro, *Biol. Reprod.*, 16, 228–237. The medium was supplemented with 0.6% bovine serum albumin, 10 mM N-2-hydroxyethylpiperazine-N'-2-ethanesulfonic acid (HEPES), 0.2 mM pyruvate, and 21.6 mM lactate, pH 7.35. References hereinafter to TALP shall be to the medium so supplemented. Collections from four separate epididymides were assessed for spermatozoan motility. The sample with the highest percent motility (60% or higher) was then evaluated for spermatozoan concentration with a hemocytometer. The final concentration of spermatozoa was $1 \times 10^8$ sperm/ml.

Rabbit spermatozoa was obtained from semen collected from New Zealand white male rabbits. Each ejaculate was examined for sperm motility, and the sperm were separated from the semen plasma and suspended in TALP by procedures comparable to those disclosed above with regard to bovine sperm. The final concentration of spermatozoa used in the assays was $1 \times 10^8$ sperm/ml.

Acrosomal staining was accomplished by the method of J. H. D. Bryan and S. R. Akruk (1977), A Naphthol Yellow S and Erythrosin B Staining Procedure for use in Studies of the Acrosome Reaction of Rabbit Spermatozoa, *Stain Technol.*, 52, 47–50. Sperm smears were made on microscope slides to be subjected to the staining procedure. A minimum of 100 sperm in each slide-mounted sample were counted by light microscopy to determine the percentage of acrosome-reacted sperm.

Alternatively, sperm were wet mounted on slides under cover slips and examined without staining. The use of microscopes capable of enhanced definition, such as microscopes equipped with Nomarski optics allows one to visually distinguish between spermatozoa that have or have not undergone an acrosome reaction. Preferably a small amount of formaldehyde was added to the sperm just prior to microscopic examination to reduce motility and thus facilitate observation.

Spermatozoa were fixed for electron microscopy by the procedure described by R. C. Jones (1973), Preparation of Spermatozoa for Electron and Light Microscopy, *J. Reprod. Fertil.*, 1933, 145–149. Vesiculation of the acrosome of the spermatozoa observed was at magnifications that ranged from 12,000× to 20,000×. As is discussed below, vesiculation is one of the recognized indicia of a normal acrosome reaction. One hundred sperm were randomly selected and examined from each sample evaluated.

To determine the ability of CS-A to induce an acrosome reaction, the epididimal bovine spermatozoa described above were incubated for 22 hours in the presence of either 0, 1, 10, or 100 μg/ml of CS-A. The samples were subjected to the acrosomal staining procedure referred to above. Sperm which accepted the stain were considered to have not undergone an acrosome reaction. To confirm the ability of the light microscopy staining method to assay the acrosome reaction, specimens of the spermatozoa before and after exposure to CS-A were examined for vesiculation of the outer acrosomal membrane. The accuracy of the interpretation of staining set forth above was proved to be accurate.

The percentages of sperm exhibiting an acrosome reaction in the presence of 0, 1, 10, or 100 μg/ml of CS-A are presented in FIG. 1. The results are expressed as the mean ± SEM from three replicates. As can be seen from FIG. 1, incubation with CS-A significantly enhanced the ability of sperm to undergo an acrosome reaction. Regression analysis showed that a significantly linear regression existed from 1 to 100 μg/ml, the equation for the regression line being $y = 12.5x + 41.6$, Fcalc=23.5; 1, 7df, $p < 0.005$. The absence of CS-A (the control) was without effect on the acrosome reaction. Viability of sperm did not differ significantly among the controls or the various doses of CS-A. Thus, staining for the acrosome reaction was not biased by the presence of dead sperm.

Electron microscopy showed that the induction of the acrosome reaction by CS-A was morphologically normal. The criteria for judging the normalcy of the acrosome reaction were those set forth by Fawcett (1975) in the publication referred to above and W. Byrd (1981), In Vitro Capacitation and the Chemically Induced Acrosome Reaction in Bovine Spermatozoa, *J. Exp. Zool.*, 215, 35–46, including vesiculation of the outer acrosomal membrane. As much as 75% of the sperm in the presence of CS-A had undergone vesiculation, whereas those sperm incubated in the absence of CS-A did not demonstrate any significant vesiculation. Fertilization experiments were conducted in vitro with sperm incubated both with and without CS-A. The differences between the control and CS-A treated spermatozoa were significant ($p < 0.01$) with sperm treated with CS-A demonstrating superior ability to penetrate and fertilize bovine ova. This indicated that the acrosomal reaction induced was at least the functional equivalent of that occurring in vitro.

By these experiments it was demonstrated that CS-A was capable of stimulating an acrosome reaction in bovine spermatozoa and that observation by light microscopy by the methods disclosed above provided a measurement of the acrosome reaction stimulated that was comparable in accuracy to that obtainable by electron microscopy. CS-A was determined to have facilitated a true acrosome reaction functionally equivalent to that occurring in vivo.

Figure 2:
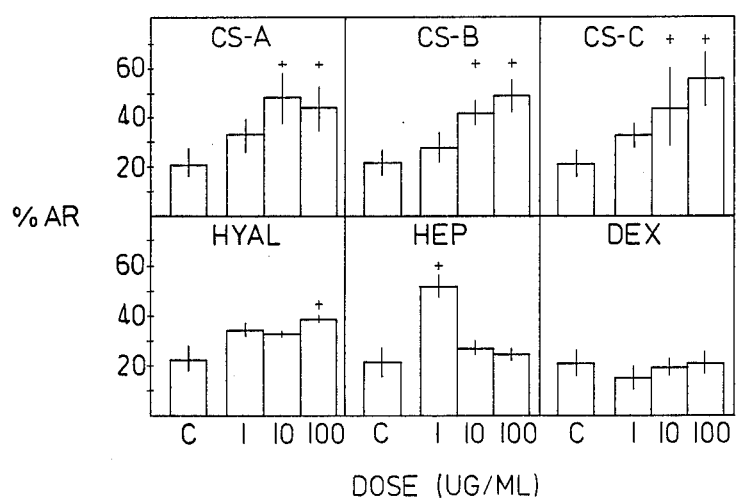

The effect of incubation with GAGs upon rabbit spermatozoa was evaluated in a separate set of experiments. Spermatozoa prepared after the method set forth above were incubated for nine hours with concentrations of 1, 10, and 100 μg/ml of each of CS-A, CS-B, CS-C, heparin, and hyaluronic acid. Control samples consisted of sperm incubated without GAGs. The results are shown in FIG. 2. The mean ± SEM is shown as calculated from three replicates in each instance. Results significantly differing from the control ($p<0.05$) are indicated in FIG. 2 with an asterisk. The results for heparin and hyaluronic acid are labeled "HEP" and "HYAL," respectively. The number of sulfate units per disaccharide unit of the various GAGs ranges from 0 for hyaluronic acid to as much as 3 for CS-B and heparin. Dextran sulfate is a sodium salt of a branched, sulfated polysaccharide and was used as an appropriate sulfated control.

The results of incubation with dextran sulfate are also shown in FIG. 2. As can be seen, incubation with dextran sulfate produced no statistically significant effect on the acrosome reaction. The extent of the acrosome reaction in each case was measured by light microscopy, using the staining method disclosed above. Once again, spermatozoa that had undergone the acrosome reaction were distinguishable from the remaining spermatozoa by their failure to take up stain. As can be seen from the results shown in FIG. 2, each GAG was capable of inducing an acrosome reaction in the rabbit sperm. However, the concentration at which the effect was most pronounced was not the same for each GAG. A comparable experiment was conducted using bovine semen and using the GAG heparan sulfate. The results were substantially the same as those achieved with heparin.

A sample of human semen was exposed to heparin in concentrations and after application of sperm isolation procedures generally the same as those described for rabbit semen, above. An acrosomal reaction was observed at corresponding heparin concentrations and comparable in all ways to that observed in rabbit semen. From this it can be seen that the reactions observed are not species specific but can be broadly generalized in mammals.

On the basis of the information acquired as a result of the experiments reviewed above, an attempt was made to evaluate the ability of spermatozoa from bulls of known fertility to undergo an acrosome reaction upon being incubated with a multi-isomeric mixture of CS-A, CS-B, and CS-C, hereinafter referred to simply as chrondroitin sulfate (CS). Eight bulls owned by a firm commercially engaged in artificial insemination were rated on the basis of the bulls' nonreturn rates, the conventional industry measurement of bull fertility. A nonreturn insemination is one in which the cow inseminated becomes pregnant upon the first effort.

The bulls were divided into a first group having a nonreturn rate in excess of 65% and a second group having a nonreturn rate less than 65%. Sperm from these bulls was prepared in the same way as the bull spermatozoa were prepared in the experiment referred to above. The sperm samples were then incubated for nine hours with CS in varying concentrations. Then the sperm were wet mounted, as is described above, and evaluated by light microscopy using a microscope equipped with Nomarski optics for evidence of having undergone an acrosome reaction. Concentrations of 0, 1, 10, and 50 μg/ml of CS were used. With increasing concentrations of CS, a linear increase in sperm perceived to have undergone an acrosome reaction resulted for each group of bulls, with the group having a nonreturn rate in excess of 65% exhibiting a higher rate of acrosome reaction.

The difference between the two groups of bulls became statistically significant ($p<0.025$) at a CS concentration of 10 μg/ml. At a CS concentration of 50 μg/ml the difference in acrosome reaction became significant with p less than or equal to 0.01. Thus, it was demonstrated that a statistically significant distinction between bulls of different fertility could be made by light microscopic direct examination of spermatozoa following treatment with CS after a period of incubation of the spermatozoa in the CS sufficient to evoke an acrosome reaction therein. Preferably the incubation period was from 6 to 9 hours, and preferably it was for 9 hours. In the experiments with rabbit spermatozoa referred to above, it was found that an incubation period in excess of 9 hours resulted in no significant additional differences between spermatozoa subjected to the various concentrations of the GAGs utilized in that experiment. Consequently, while a somewhat longer incubation period should not be harmful, it is believed to have no additional value.

From the results of the bovine, rabbit, and human spermatozoa experiments disclosed above, it will be apparent that the GAGs tested are effective in selected amounts to induce acrosomal reactions in mammalian sperm. Furthermore, there is a direct relationship between the occurrence of this reaction in sperm from a given animal and the ability of that sperm to fertilize an ovum. Thus, a general method for evaluating the fertility of a male mammal is indicated. First a semen sample must be obtained from the individual to be tested. Then, the sperm of the sample must be separated from the semen plasma, preferably by the dilution and centrifugation techniques described above. Test and control portions of sperm are then isolated and incubated for a selected length of time. The test portion is exposed to a GAG in a concentration effective to induce an acrosomal reaction in sperm. The concentration of GAG relative to the sperm must correspond in the incubated test portions for comparisons of fertility between tested semen samples to be reliable. To that end, sperm concentrations of the separated sperm are determined by conventional means prior to the isolation of test and control portions and dilutions are made to adjust sperm concentrations. Preferably a sperm concentration of $5 \times 10^7$ to $1 \times 10^8$ is used. Preferably the GAG is selected from the group consisting of chondroitin sulfate A, B, or C or a combination thereof, heparin, heperan sulfate, hyaluronic acid and combinations thereof.

Conventional means for determining sperm concentrations include the dilution of a known volume of semen with a known volume of normal saline. The turgidity of the diluted sample is then determined spectrophotometrically, from which determination concentration may be calculated. Alternatively, direct visual counts may be made by means of a hemacytometer after a comparable preparation of a sample by dilution.

Alternatively, a sample of semen from a first individual and of a known volume simply may be presumed to contain approximately the same number of sperm as a like volume of sperm from a second individual. With individuals otherwise comparable, that presumption yields useful results in comparing their fertility, although the method so performed is less accurate than when a more sophisticated method of determining sperm concentration is employed.

A representative sample of the sperm from each portion is then counted by means of observation by light microscopy to measure the percent increase in acrosome reaction in the test portion as compared to the control portion. In comparing two semen samples, that sample in which a larger percent increase in acrosome reaction is observed may be predicted to be more capable of impregnating females than the other sample, all other factors held constant. Preferably data on a large number of animals of a given type will have been collected so that an animal to be tested may be compared to a norm or a desired superior performance. It is also preferred to prepare multiple test portions of sperm, each incubated with a different GAG concentration. By that means it is possible to detect anomalies arising from unexpected effects of GAG concentrations or unusual individual characteristics of the animal being tested.

The kit of the invention is adapted to facilitate performing the method of the invention. The kit includes a supply of a sterile culture medium, preferably TALP. The TALP may either be made up in aqueous solution or may be the soluble ingredients of TALP in dry form and adapted to be reconstituted by the addition of sterile water. In such an event distilled water of neutral or very slightly acidic pH should be used. Water may be provided as part of the kit whereby the sterility and the pH of the water used in the TALP may be controlled and be consistent from kit to kit. Alternatively, water may be obtained separately by the user of the kit, sterilized, and added to the soluble ingredients to form the supply of sterile TALP. An appropriate, conventional millipore filter may be provided through which unsterilized water may be directed into a suitable, sterile container containing the dry soluble ingredients in order to sterilize the water. For such an arrangement and in other instances, it is convenient to supply the dry ingredients in a bottle or other container of a standard size and with an amount of dry ingredients sufficient that the container may simply be filled with sterile water and agitated to produce the desired quantity of TALP.

The kit further includes sterile, closeable culture vessels including at least one control and one test vessel. Additionally, a supply of a selected, sterile GAG or combination of two or more GAGs is included in the kit. Means are provided for metering substantially aseptically a known amount of GAG into each test vessel. Preferably there are at least three test vessels and amounts of GAG are so measured or metered into them as to result in final, distributed, selected GAG concentrations within the range of approximately 1 to 250 $\mu g/ml$ upon addition of sperm suspended in a measured amount of TALP. In the preferred embodiment of the kit, premeasured amounts of GAG are contained in each of the test vessels, with the GAG so measured as to result in the indicated GAG concentrations upon addition of a known and convenient amount of TALP. Ultimate GAG concentrations of 1, 10, and 50 $\mu g/ml$ are considered convenient. Preferably the GAG is dry, to be dissolved in TALP in which the sperm to be tested are suspended. Alternatively, the GAG may be dissolved in a measured amount of TALP.

Many facilities for artificial insemination are equipped with reasonably sophisticated laboratories including facilities sufficient for the separation of sperm from sperm plasma in accord with the method disclosed above. The supply of sterile TALP provided as part of the kit may be used in that process. Preferably the sperm so separated from the sperm plasma are resuspended in TALP at a concentration such that a known amount of the sperm suspension may be added to each culture vessel to result in control and test portions of known concentration and preferably of a sperm concentration of $5 \times 10^7$ to $1 \times 10^8$ sperm per milliliter.

When GAG has been supplied to the test vessels in dry form, as is discussed above, the sperm suspension is made up to the desired final concentration and metered amounts of the suspension are added to each culture vessel so as to result in the desired concentrations of GAG. A sterile, calibrated syringe may be conveniently used to measure and transfer the sperm suspended in TALP. However, sperm are delicate and, if subjected to excessive fluid turbulence, may be broken into pieces and killed. Consequently, it is preferred that no part of the syringe or any needle attached thereto through which the sperm suspension must pass be smaller than the lumen of an 18 gauge needle. When such a syringe equipped with a needle is used as a means for metering a known amount of sperm into each culture vessel, a convenient alternative embodiment of the kit includes culture vessels closed with a needle puncturable plug. The sperm suspended in TALP may then be introduced conveniently into the culture vessels directly through the puncturable plug without any need to open the culture vessel, facilitating avoidance of microbiological contamination of the culture vessel.

It is understood that the present invention is not limited to the particular materials, stains, and steps disclosed herein. Thus, exact concentration of reagents, incubation times, selection of stains, and the like may be adjusted, and substitutions may be made as will be apparent to those skilled in the art, all within the spirit and scope of the invention. Rather than being so limited, the invention embraces all such modified forms thereof as come within the scope of the following claims.

What is claimed is:

1. A method for evaluating the fertility of a first male mammal with reference to the fertility of at least one reference male mammal comprising the steps of:
   (a) obtaining a semen sample from the first male mammal;
   (b) separating the sperm from the seminal plasma of the semen sample;
   (c) isolating at least one test portion and a control portion of the sperm;
   (d) incubating the portions of sperm, exposing the test portion to a glycosaminoglycan in a concentration effective to induce an acrosome reaction in sperm;
   (e) counting a representative sample of incubated sperm from each portion to measure the increase characteristic of the first male mammal in acrosome reaction in the test portion as compared to the control portion;
   (f) obtaining a semen sample from the reference male mammal and subjecting it to the same steps of separating, isolating, incubating, and counting to which the semen sample of the first male mammal was subjected to measure the increase characteristic of the reference male mammal in acrosome reaction in the test portion as compared to the control portion of the sperm of the reference male mammal; and
   (g) comparing the increase in acrosome reaction characteristic of the first male mammal with the increase in acrosome reaction characteristic of the reference male mammal, whereupon the fertility of the first male mammal may be determined to be greater or lesser than that of the reference male mammal as the increase in acrosome reaction characteristic of the first male mammal is found to be greater or lesser than the increase in acrosome reaction characteristic of the reference male mammal.

2. The method of claim 1 wherein the step of separating the sperm from the seminal plasma includes diluting the semen with a selected culture medium and centrifuging the diluted semen to separate the spermatozoa therefrom and resuspending the sperm in the culture medium at a selected concentration of sperm.

3. The method of claim 1 wherein the glycosaminoglycan is selected from the group consisting of heparin, heperan sulfate, chondroitin sulfate A, chondroitin sulfate B, chondroitin sulfate C, hyaluronic acid, and any mixture thereof.

4. The method of claim 3 wherein the glycosaminoglycan is selected from the group consisting of chondroitin sulfate A, chondroitin sulfate B, chondroitin sulfate C, and any mixture thereof, in a concentration not less than 10 $\mu$g/ml.

5. The method of claim 3 wherein the glycosaminoglycan is hyaluronic acid in a concentration not less than 100 $\mu$g/ml.

6. The method of claim 3 wherein the glycosaminoglycan is selected from the group consisting of heparan sulfate and heparin in a concentration of approximately 1 $\mu$g/ml.

7. The method of claim 3 wherein the step of incubating the portions of sperm, exposing the test portion to a glycosaminoglycan includes incubating the portions of sperm for not less than approximately six hours.

8. The method of claim 1 wherein:
the step of isolating at least one test portion and a control portion of the sperm includes isolating a plurality of test portions; and wherein
the step of incubating the portions of sperm, exposing the test portion to a glycosaminoglycan, includes exposing test portions to differing concentrations of the glycosaminoglycan.

9. The method of claim 1 wherein the increase in acrosome reaction characteristic of reference male mammals has been measured for a number of such male mammals sufficient that a norm has been established, whereupon the fertility of the first male mammal may be evaluated with reference to that norm.

* * * * *